(12) United States Patent  
Holmes

(10) Patent No.: US 9,237,980 B2  
(45) Date of Patent: Jan. 19, 2016

(54) GARMENT FOR THERAPEUTIC TREATMENT

(71) Applicant: Jobskin Limited, Long Eaton, Nottingham (GB)

(72) Inventor: Rachael G. Holmes, Long Eaton (GB)

(73) Assignee: JOBSKIN LIMITED, Long Eaton, Nottingham (GB)

( * ) Notice: Subject to any disclaimer, the term of this patent is extended or adjusted under 35 U.S.C. 154(b) by 0 days.

(21) Appl. No.: 14/260,471

(22) Filed: Apr. 24, 2014

(65) Prior Publication Data

US 2014/0323932 A1    Oct. 30, 2014

(30) Foreign Application Priority Data

Apr. 24, 2013 (GB) .................................. 1307348.1

(51) Int. Cl.
| | |
|---|---|
| *A61H 1/00* | (2006.01) |
| *A41F 1/00* | (2006.01) |
| *A61F 13/14* | (2006.01) |
| *A61F 13/00* | (2006.01) |

(52) U.S. Cl.
CPC ........ *A61H 1/008* (2013.01); *A41F 1/00* (2013.01); *A61F 13/14* (2013.01); *A61F 2013/0028* (2013.01)

(58) Field of Classification Search
CPC ..... A41D 13/0015; A41D 3/00; A41D 13/02; A41D 13/1236; B63C 11/04; A41F 1/00

USPC ........... 2/69, 2.17, 79, 108, 96, 75, 114, 913, 2/80

See application file for complete search history.

(56) References Cited

U.S. PATENT DOCUMENTS

| | | | | |
|---|---|---|---|---|
| 2,738,512 | A * | 3/1956 | Winer ................................. | 2/80 |
| 3,555,567 | A * | 1/1971 | Owen ............................. | 2/69.5 |
| 3,769,634 | A * | 11/1973 | Florens, Jr. ............... | A41F 1/00 |
| | | | | 2/106 |
| 5,040,526 | A | 8/1991 | Erickson | |
| 5,058,208 | A * | 10/1991 | Adams ............................... | 2/80 |
| 5,153,938 | A * | 10/1992 | Epperson ......................... | 2/2.14 |
| 8,281,418 | B2 * | 10/2012 | Cohen, Jr. ............ | A41D 13/015 |
| | | | | 2/465 |
| 2011/0264021 | A1 | 10/2011 | Hettich | |

FOREIGN PATENT DOCUMENTS

| | | |
|---|---|---|
| WO | 2007065435 A1 | 6/2007 |
| WO | 2007112494 A1 | 10/2007 |

* cited by examiner

*Primary Examiner* — Tejash Patel  
(74) *Attorney, Agent, or Firm* — Young Basile

(57) ABSTRACT

A medical compression suit has first and second elongate openings and first and second fasteners for releasably closing the first and second elongate openings respectively such that releasing the fasteners allows the openings to be opened, facilitating the donning and doffing of the suit by a wearer, the first and second openings being provided on the front or the rear of the suit.

18 Claims, 3 Drawing Sheets

GARMENT FOR THERAPEUTIC TREATMENT

TECHNICAL FIELD

The present invention relates to garment for use in the physical therapy of patients. In particular, the invention relates to a suit or other garment for providing dynamic compression to the body of a wearer.

BACKGROUND

It is known to use a suit to apply dynamic compression to patients for a range of medical conditions. The use of such garments can increase sensory and proprioceptive feedback as well as provide musculoskeletal support and can assist and lead to motor learning and neural integration.

Such suits give the wearer constant, consistent compression and support. This improves posture, positioning and function.

The constant compression means that the suits cling tightly to the wearer's body. Due to the required tension in the fabric it is difficult for wearers to put on (don) and take off (doff) the suit. Known dynamic compression suits seek to permit donning and doffing by providing an elongate slit in the front or rear of the suit. The slit is provided with a zip for closing the slit. However the tight fit of the suit means that a significant freedom of movement is required, including flexion, extension and rotation of the limbs and torso, in order to don/doff the suit, often requiring the assistance of a carer. As such the donning/doffing of suits can cause distress and even pain to a wearer, particularly for some medical conditions for which the suit is intended to be used.

It is also necessary for the suits to fit the particular wearer's body to a high degree of accuracy in order to achieve the desired clinical goals. If the suit is too small, it may be uncomfortably tight (or harmfully so). If the suit is too large, it may not provide the desired therapeutic effects. This is presently addressed by providing made-to-measure suits to improve the accuracy of the fit. However the shape of a wearer's body, particularly children, may change over time, thus necessitating corresponding changes to the dynamic compression garment.

A further problem resulting from the tightness of the suits is that the fasteners have been found in some instances to cause discomfort to the wearer.

SUMMARY

The present invention overcomes or substantially mitigates some or all of the above mentioned and/or other disadvantages associated with the prior art.

According to a first aspect of the invention, there is provided a medical compression garment for providing musculoskeletal support, the garment having a central axis and comprising first and second fasteners, the fasteners being elongate in form and offset from the central axis so as to define an intermediate panel of said garment therebetween, said intermediate panel being openable by releasing the fasteners to facilitate donning and doffing of the garment by a wearer.

The garment may comprise an orthosis, such as a sensory orthosis garment.

The garment typically has front and rear portions, which may comprise front and rear panels. The first and second fasteners may be provided on the front panel and/or the rear panel of the garment.

The arrangement provided by the invention allows the garment to be opened to a greater extent than known suits. This enables the garment to be donned and doffed more easily. This is particularly useful for medical compression suits as such suits are, by design, tight on the wearer's body.

The garment may be arranged to surround the torso of a wearer. The garment may be arranged to surround a portion of the torso, such as the abdomen or thorax, or else the entire torso. The garment may be arranged to surround at least a portion of the leg or arm of the wearer, such as a thigh or upper arm region. The garment may have sleeve and/or leg portions. The garment may be sleeveless, for example, at least in part having the shape of a vest.

The garment may be a suit.

The garment may comprise a first opening, for example at an end of the garment. Either or both of the first and/or second fasteners may terminate at the first opening. The garment may have one or more further openings. Either or both of the first and second fasteners may terminate at one or more of the further openings. The fasteners may extend between the first and the one or more further opening.

The first opening may be a neck opening. The first and second fasteners may terminate at spaced locations at the edge of the first opening.

The first and/or second fasteners may extend the full length of the garment. This increases the extent to which a suit can be opened and hence makes donning and doffing easier.

The angle formed between the first and second fasteners may be less than 20°, and typically less than 15° or 10°. The first elongate fastener may be generally parallel to the second elongate fastener.

The spacing between the first and second fasteners may be greater than 3 or 5 cm. A minimum spacing may occur at the edge of the first opening. The first and second fasteners may be spaced apart by a distance of between 6 and 20 cm, typically between 8 and 15 cm, over a major portion of the garment length. Such a spacing may be maintained for example over an abdominal region of the garment.

The central axis may be a longitudinal or major axis of the garment. The first and/or second fasteners may be arranged on either side of the central axis. This enables the provision of an arrangement in which the first and/or second fasteners are remote from the spine of the wearer in use, and as a result the suit is more comfortable. The first and/or second fasteners may be equidistant from the central axis. The first and/or second elongate openings may be inclined relative to the central axis. The intermediate panel may be tapered.

The first and/or second fastener may comprise two, typically opposing, fastening members. The fastening members may be connected to opposing edges of adjacent panels of material. The fastening members may join one or more flanking panels to the intermediate panel, for example to opposing sides/edges of the intermediate panel. The fastening members may be connected to the corresponding panel by stitching. The first and or second fasteners may be zip fasteners. Each row of teeth of the zip fastener may be connected to an edge of the respective panel and extend along the edge.

The zip fasteners may extend along the full length of the respective panel(s). This enables the openings to be full closed in use. In some embodiments, the zip fasteners are arranged such that both the first and second zip fasteners are unfastenable by moving a runner generally upwardly or generally downwardly (i.e. in a first direction). In alternative embodiments, the zip fasteners are arranged such that one of the first and second zip fasteners is unfastenable by moving its runner in a first direction, and the other is unfastenable by moving its runner in a second, typically opposing, direction.

The garment may be provided with a third elongate fastener, located on the opposite side of the garment to the first and second elongate openings. This further facilitates donning and doffing of the suit. A fourth elongate fastener could also be provided on the same side as the third fastener but spaced therefrom, for example in the manner of the first and second fasteners.

An opening, such as a cut out, may be provided in a crotch region of the garment. This may provide a second opening. The first and/or second fasteners may extend to, or beyond, the crotch opening. A third fastener may extend from the first opening (i.e. a neck region of the garment) to the cut out in the crotch region. This enables a suit to be opened to a greater extent. The third fastener may be a third zip fastener.

The garment has a protective layer located, in use, between the wearer's body and any, or any combination of, the fasteners. The protective layer may be a strip of material and may extend along the length of the respective zip fastener. The protective strip may be attached to the interior surface of the garment, preferably by stitching. The protective strip may extend around an edge of an opening in the garment and onto an external surface of the garment. This may alleviate irritation to the wearer given the tight fir of the suit.

An auxiliary fastener may be provided in the vicinity of any or any combination of the fasteners described above. The first and/or second fastener may be selectively connectable to an auxiliary fastener, e.g. to close the garment. Doing so may provide a different degree of tightness or fitment of the garment.

The auxiliary fastener may be selectively connectable to one of the fastening members of the first or second fastener. The first fastening member may be connectable to the auxiliary fastener instead of the second fastening member. The auxiliary fastener may be an auxiliary fastening member. The auxiliary fastener may extend in substantially the same direction as the first and/or second fastening member. If the first or second fastening members are zip fasteners, the auxiliary fastener comprises a single row of teeth. The auxiliary fastener may be connected to an exterior surface of the suit, preferably by stitching. The auxiliary fastener extends parallel to the first or second fastener. Auxiliary row of teeth can be engaged with a runner of a fastening member such that moving the runner along the track of the zip causes the teeth of the first or second fastener to mesh with the teeth of the auxiliary fastener to close the opening.

In alternative embodiments the auxiliary fastener is provided with a runner. In these embodiments, a row of teeth from the first or second fastener can be engaged with the runner of the auxiliary zip to enable the respective opening to be closed.

The garment may comprise elastic fibres. The elastic fibres may constitute between approximately a quarter and a third of the material composition. The garment may be substantially formed of synthetic, e.g. polymer, fibres. The garment may comprise elastane, such as Lycra® or alternatives thereof. The garment may comprise two-way stretch fabric, e.g. a polyamide fabric, such as a power net fabric. The use of such fabrics in Dynamic compression garments may provide therapeutic benefits for patients having any of the following conditions: Cerebral Palsy, Acquired Spinal Injury, Cerebellar Ataxia, Spina Bifida, Cerebral Vascular Accident/Stroke, Multiple Sclerosis, Dystonia. A Polycotton Lycra® may be used.

The garment may be adapted such that, in use, the suit applies a compressive force to the wearer's body. If the suit has sleeves, then, in use, the sleeves extend as far as a part of the wearer's arm between the shoulder and the elbow. The sleeves may extend to approximately a mid-point between the shoulder and the elbow. The sleeves may be connected to the remainder of the suit by stitching. The suit may comprise leg portions which may connect to the remainder of the suit by stitching. In use, the leg portions may extend to as far as the thigh of the wearer, and preferably as far as approximately the mid-point between the wearer's waist and knee. The first and/or second fasteners may extend from the vicinity of the collar of the suit to the bottom of the leg portion. This means that the wearer does not have to "step into"/"step out of" the suit when donning/doffing the suit. Instead, the suit can be wrapped around the wearer and then fastened. In view of the intrinsic tightness of medical compression suits, this greatly facilitates donning and doffing of the suit.

The suit may have one or more reinforcing layer portion. The reinforcing layer may be formed in an elastic fabric having a lower fabric weight/density than the fabric from which a remainder of the garment is formed, such as for example the fabric of the garment panels. The reinforcing layer may be connected to an exterior surface of the suit, and is preferably connected thereto by stitching. The reinforcing layer may be present on the rear of the suit and/or one or both leg portions. If the reinforcing layer is present on the rear of the suit, it may cover substantially the whole of a torso portion of the rear of the suit, e.g. from the wearer's waist upwards. If the reinforcing layer is present on the leg portions of the suit, it may cover a region of the leg portion that faces generally outwardly (i.e. away from the central axis) in use.

BRIEF DESCRIPTION OF THE DRAWINGS

Preferred embodiments of the invention will now be described in detail, with reference to the accompanying drawings, in which.

DETAILED DESCRIPTION OF THE EMBODIMENTS

Figure 1:
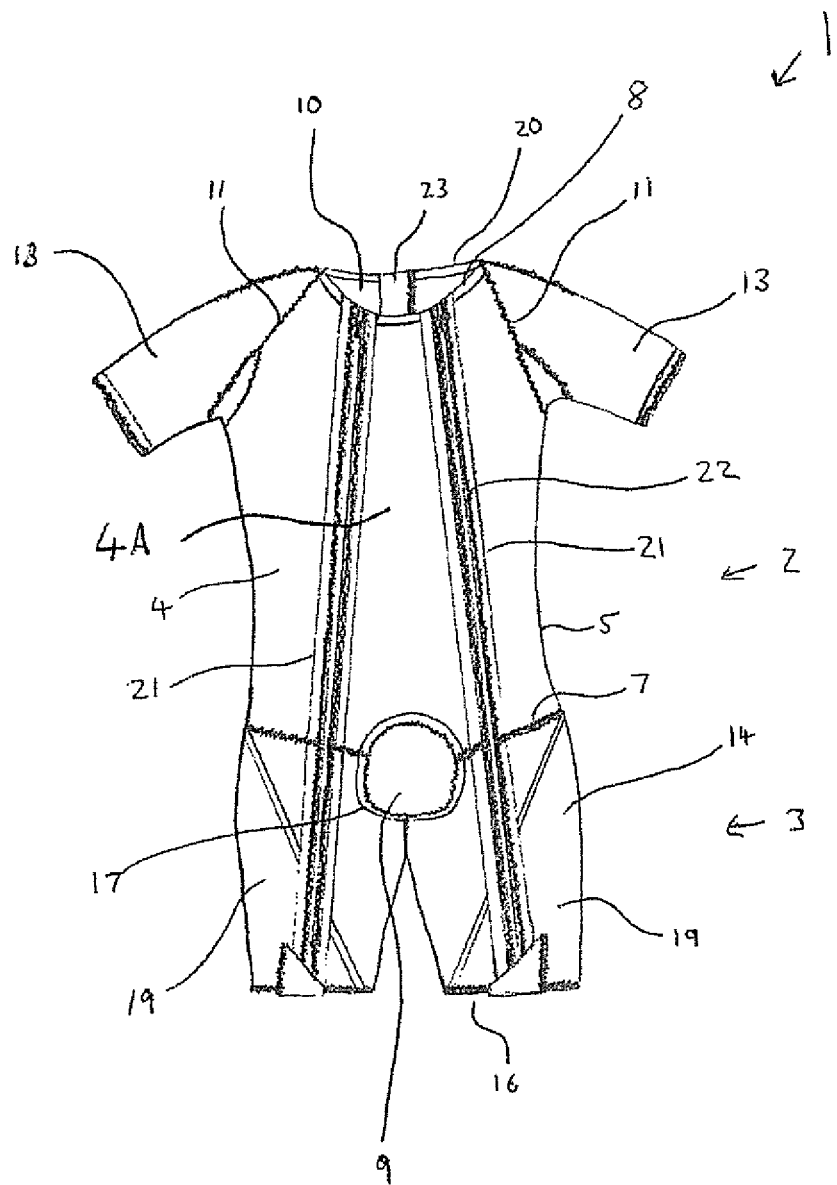
FIG. 1 is a front view of the suit according to a first embodiment of the invention.

Multiple embodiments of the invention will be described. For expediency, the features common to those embodiments will be described first, followed by the differences therebetween.

The suit of the invention, generally designated 1 has the general appearance of a leotard or closely-fitted tunic. The suit comprises upper 2 and lower 3 body portions, see FIG. 1.

The upper body portion 2 comprises a front wall 4. The front wall 4 has side edges 5 extending generally vertically but with a slight outward taper from bottom to top. The lower end of the front wall has a central, generally arcuate or semi-circular recess 6 defining part of a crotch opening 9. A lower edge 7 of the front wall 4 extends between the recess 6 and each of the side edges 5. Each lower edge 7 is inclined to the horizontal such that it subtends an obtuse angle to the respective side edge 5.

The upper end of the front wall 4 has a central, generally arcuate, e.g. a circular segment or semi-circular, recess 8 defining part of a neck opening 10 or neckline. The upper end of the front wall 4 has inclined edges 11 extending between the recess 8 and each of the side edges 5. Each inclined edge 11 is inclined to the horizontal such that it subtends an obtuse angle to the respective side edge 5.

Figure 2:
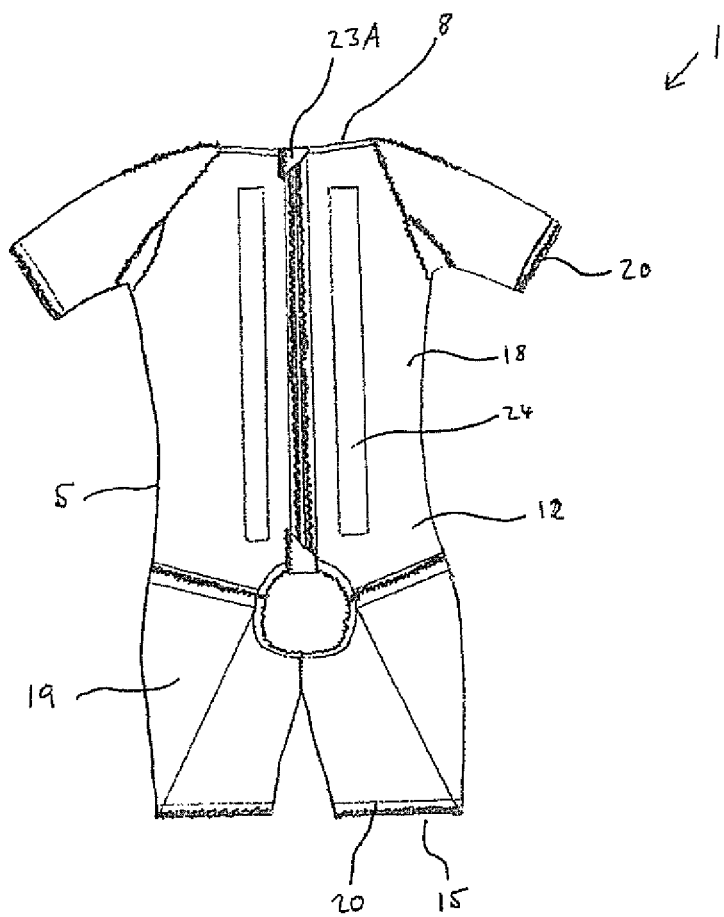
FIG. 2 is a rear view of the suit according to a first embodiment of the invention; and, FIG. 3 is a front view of the suit according to a second embodiment of the invention.

FIG. 2 shows the suit of the invention from the rear. There is a rear wall 12 that is of substantially the shape as the front wall 4 except that the recess 8 partly defining the collar portion is shallower and that the rear wall 12 is slightly thicker than the front wall 4. The side edges 5 of the rear wall are stitched to the side edges 5 of the front wall 4.

The inclined edges 11 at the upper end of the upper body portion 2 are provided with arm portions 13 (see FIG. 1). The arm portions 13 have the form of sleeves. Each arm portion 13 is stitched to a respective inclined edge 11. The arm portions 13 are short, such that they cover the shoulder of the wearer and part of the upper arm but terminate above the elbow. The diameter of the arm portion 13 at its open end may be approximately 8 cm for a child's suit but may be enlarged or reduced in dimension as required for a close fit. Please note that the second embodiment of the invention (described below), does not include arm portions. The arm portions 13 are therefore not common to all the embodiments.

The lower body portion 3 comprises two leg portions 14. Each leg portion 14 is generally tubular or sleeve-like in form. Each leg portion 14 is formed from a single piece of material, the opposite ends of which are stitched together. The width of the leg portion 14 increases from bottom to top to induce a slight taper. The lower opening 15 of the leg portion 14 has a diameter of approximately 10 cm. The lower edge 16 of the leg portion 14 extends generally horizontally. The upper end of the leg portion 14 is inclined to the horizontal to match the inclination of the corresponding inclined lower edge 7 of the upper body portion 2. A curved recess 17 is defined in the upper inside corner of the leg portion 14 in order to define part of the crotch opening 9. The profile of the curved recess 17 of each leg portion 14 matches that of the curved recess 6 on the lower edge of the upper body portion 2, so that together they define the crotch opening 9.

Both the upper 2 and lower 3 body portions are formed of a Polycotton Lycra. Typically those portions are formed of a plurality of panels stitched together at their opposing edges. The specific material used may have a composition of 51% Polyamide, 32% Elastane and 17% Cotton, although variations of composition are possible provided that greatest to smallest proportion of material remains in the order Plolyamide, Elastane, Cotton. The material weight may be between 270 and 300 grams per square meter (gsm) dependent on the strength requirements.

The material may be a knitted fabric and may allow stretch on the warp of between 90% and 105%, potentially subject to a standard tolerance. In the example given, for a 275 gsm fabric, the stretch on the warp is 105%. The stretch on the weft may be between, for example, 65% and 80%, potentially subject to a standard tolerance, with the value being approximately 75% for this example.

A reinforcing web or layer 18 is stitched over the exterior surface of the rear wall 12 of the upper body portion 2. The reinforcing layer 18 covers the whole of the exterior surface of the rear wall 12 of the upper body portion 2. Furthermore, a reinforcing web or layer 19 portion is stitched to the exterior surface of each leg portion 14. The reinforcing layers 19 are rectangular and extend generally downwardly from the inclined upper edges at the top end of the lower body portion. The inclination of the reinforcing layers 19 matches that of the inclined upper edges at the top end of the lower body portion 3. The reinforcing layers 18 and 19 are formed of a Lycra/Polyamide powernet having a less dense composition than the material from which the underlying panels are formed.

The reinforcing material has a two-way or multidirectional stretch and may have a material weight of approximately 200-230 gsm, with this particular example being 220 gsm. The composition may be entirely synthetic and may comprise a majority of Polyamide and a minority of Elastane. In this example the composition is approximately 75% polyamide and 25% Elastane.

All of the openings in the suit, i.e. the openings at the neck 10, the crotch 9, the arm portions 13 and the leg portions 14, have a strengthening band 20 stitched around the inside of the opening. This is shown most clearly in FIG. 2. The band 20 has a width of approximately 1.5 cm.

The suit 1 is approximately 60 cm long from top to bottom. The distance between the open ends of the arm portions 13 is approximately 48 cm. The maximum width of the suit 1, excluding the arm portions 13 is approximately 27 cm. However it will be appreciated that any dimensions may change to accommodate different sizes. The suit is particularly intended to be worn by children.

The specific embodiments of the invention will now be described. In the first embodiment, two slits 21 are provided in the front wall 4 of the suit 1. The slits 21 facilitate donning and doffing of the suit 1. One slit 21 extends from the lower edge of each leg portion 14 to the collar opening 10 on the upper body portion 2. The slits 21 are generally straight and are slightly inclined to the vertical, such that the separation of the slits 21 in the region of the collar 10 is approximately 6 cm and the separation of the slits 21 in the region of the crotch 9 is approximately 11 cm.

A zip formation 22 is located at each slit 21 to allow selective opening and closing of the slits. As is conventional, each zip formation 22 comprises two rows of teeth that are meshed together to form a track when a runner is moved along the track. Each row is affixed along one of the opposing edges of the slit 21 and is typically mounted on a mounting strip (not shown). Each mounting strip is stitched to the interior surface of the suit 21, in the region of the slit 21, such that the teeth of the zip 22 are visible between the edges of the slit 21. The zip formation 22 is orientated such that the runner is moved upwardly to fasten the zip and downwardly to unfasten the zip. A zip of this orientation will be referred to below as an "upright zip". A protecting strip 23 is stitched to the inside surface of the suit 1 along the edge of the slit 21. The strip 23 covers the zip formation 22, protecting the body of the wearer from it.

The portion of the suit 1 located between the zip formations 22 comprises an intermediate panel 4A extending between the neckline 8 and the crotch opening 9. The intermediate panel is formed of a more elastic or stretchable material than the material(s) of the remainder of the suit 1. For example the intermediate panel may comprise a greater percentage of Elastane but may otherwise be similar to that described above. The increased elasticity or reduced stiffness/resilience of this panel 4A between the elongate zip formations 22 has been found to be particularly beneficial in tailoring the garment for medical compression, whilst also accommodating small changes in the weight of a wearer and/or avoiding discomfort to a wearer whilst eating or digesting food.

A slit 21 having a zip formation 22 is also provided on the rear of the suit 1, see FIG. 2. This zip formation 22 is structurally the same as the zip formation 22 on the front of the suit 1. The zip formation 22 on the rear is an upright zip and extends from the crotch opening 9 to the neck opening 10.

A protective strip 23 is stitched to the interior surface of the rear wall to protect the wearer's body from the zip formation 22. Each of the front and rear protective strips 23 have an end portion 23A which extends onto an outer face of the suit, over an end of the respective zip. The end portion 23A has an oblique terminal edge to allow easy access to the zip therebehind as necessary.

A further strengthening strip 24 is provided on either side of the slit 21 on the rear of the suit 1. Each strip 24 is stitched to the outer surface of the reinforcing layer 18. The strips 24 are generally rectangular and extend generally vertically. These strips further reinforce the suit adjacent the zip.

Figure 3:
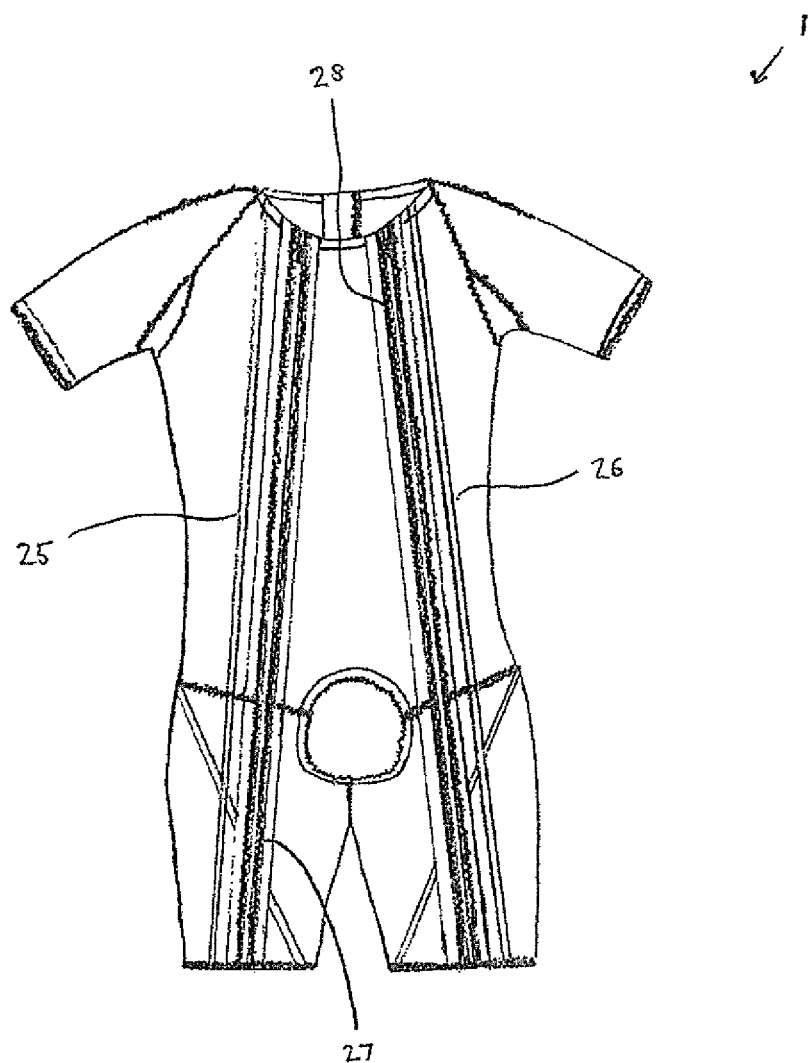

A second embodiment of the invention will now be described. FIG. 3 shows the second embodiment when viewed from the front. The rear view of the second embodiment is not shown in the Figures. The second embodiment of the invention is very similar to the first embodiment. The principal differences between the two embodiments relate to the zip arrangement. As in the first embodiment, the front of the suit 1 has two upright zips 22 extending from the lower edge of the respective leg portion 13 to the collar portion 10 and the rear of the suit 1 has a centrally located, single, upright zip 22 extending from the crotch 9 to the collar 10.

However, in the second embodiment each zip formation 22 is provided with an auxiliary zip 25, 26 (shown schematically in FIG. 3). The auxiliary zips 25, 26 are located on the front surface of the suit 1, outwardly of the two zips 22 already discussed, such that there is a left hand auxiliary zip 25 and a right hand auxiliary zip 26. For clarity, the original zips 22 will be referred to here as the primary zips 27, 28 (left hand primary zip 27 and a right hand primary zip 28).

Each auxiliary zip 25, 26 comprises a single row of teeth mounted on a mounting strip (i.e. one half of a combined zip arrangement). Each mounting strip is stitched to the outer surface of the suit, outwardly of the respective primary zip. Each auxiliary zip 25, 26 extends in a direction parallel to its respective primary zip 27, 28.

In use, the primary zips 27, 28 may be unfastened such that its row of teeth is disengaged with its runner. In the case of the left hand primary zip 27, the row of teeth of its auxiliary zip 25 can be engaged with the runner of the primary zip 27. The left hand primary zip 27 can then be fastened, resulting in the suit 1 having smaller lateral dimensions (i.e. providing) a tighter fit to the wearer's body. In the case of the right hand primary zip 28, the right hand auxiliary zip 26 has its own runner. The row of teeth which the runner of the right hand primary zip 28 can be disengaged from its runner, that row of teeth can be engaged with the runner of the right hand auxiliary zip 26. The right hand primary zip 28 can then be fastened and the suit 1 will have a tighter fit to the wearer's body. In this way, the auxiliary zips 28, 29 permit different degrees of tightness to be obtained.

In further embodiments, the upper body portion 2 need not be provided with sleeve portions 13 but may instead have shoulder straps. Furthermore, instead of inclined edges 11 at the upper end of the upper body portion 2, there may be provided curved recesses defining arm holes.

In any embodiment, the pair of spaced zip formations may be provided on the rear of the garment and a single zip may be provided on the front.

In any embodiment, the single zip may be avoided such that the suit is openable only by way of the pair of spaced zip arrangements on either the front or rear thereof. Alternatively the pair of spaced zips may be provided on both the front and rear of the garment. Furthermore, when the suit 1 of FIG. 3 is viewed from the front, the left hand zip is an upright zip, i.e. for which the runner terminates at the upper end of the zip in a closed condition, and the left hand zip is an inverted zip, i.e. for which the runner terminates at the lower end of the zip in a closed condition. Thus the zips in different embodiments may be unzipped in the same or opposing directions depending on requirements.

In any embodiment, the intermediate panel 4A is beneficial in that it can relieve pressure on the wearer's abdomen, if provided on the front wall 4, or else the wearer's spine, if provided on the rear wall. This relief of pressure can be allowed without comprising the intended function of the garment and has been found to be beneficial in reducing discomfort, for example by relieving pressure on the stomach and easing digestion.

Whilst the above examples comprise a crotch opening 9, other examples of the invention may comprise a closed crotch. In such examples, the crotch material may be of increased elasticity and/or reduced resilience compared to a majority of the garment. For example the crotch region may comprise an extension of the intermediate panel 4A or may comprise a further material region of material similar to that of intermediate panel 4A.

Orthotic garments according to examples of the present invention are used to provides dynamic compression to increase sensory and proprioceptive feedback of a wearer as well as provide musculoskeletal support. Such garments can assist and lead to motor learning and neural integration. Through the use of an orthosis providing constant, consistent compression, stretch, support and sensory information the wearer may be given the effect of therapeutic handling for the time that the garment is worn. Wearing a garment of this kind can lead to an improvement in positioning, posture and function because it provides musculo-skeletal alignment, postural stability and sensory feedback. This is thought to be due to the stimulation of the somatosensory and musculo-skeletal systems which give changes in tone and postural alignment.

The invention claimed is:

1. A medical compression garment comprising:
a compression suit configured to provide musculoskeletal support to a wearer and arranged to surround a torso of the wearer and at least a portion of the leg of the wearer and having a central axis; and
first and second fasteners configured in elongate form and extending from a neck opening to a leg opening of the garment offset from the central axis so as to define an intermediate panel of the garment between the first and second fasteners, the intermediate panel being openable by releasing the first and second fasteners to facilitate donning and doffing of the garment by the wearer.

2. The medical compression garment as claimed in claim 1, wherein the first fastener extends in generally a same direction as the second fastener.

3. The medical compression garment as claimed in claim 1, wherein at least one of the first and the second fasteners extends a full length of the garment.

4. The medical compression garment as claimed in claim 1, wherein the central axis extends from a neck region to a crotch region of garment and the first and the second fasteners are located on either side of the central axis.

5. The medical compression garment as claimed in claim 1, wherein at least one of the first and the second fasteners are zip fasteners.

6. The medical compression garment as claimed in claim 1, wherein a cut out or elastic material is provided in a crotch region of the garment.

7. The medical compression garment as claimed in claim 1, wherein the garment has one or more reinforcing layer portions located on an external surface of the garment.

8. The medical compression garment as claimed in claim 1, wherein an auxiliary fastener is provided parallel to and in a vicinity of at least one of the first and the second fasteners and the at least one of the first and the second fastener is compatible with the auxiliary fastener and selectively connectable to the auxiliary fastener, to close the garment.

9. The medical compression garment as claimed in claim 8, wherein the auxiliary fastener comprises a single row of teeth.

10. The medical compression garment as claimed in claim 1, wherein the garment is substantially formed of a powernet material.

11. The medical compression garment as claimed in claim 1, wherein the garment is substantially formed of a material of weight between 270 and 300 gsm.

12. The medical compression garment as claimed in claim 1, wherein the garment is substantially formed of a material that allows at least one of a stretch on a warp of between 90% and 105% and a stretch on a weft between 65% and 80%.

13. The medical compression garment as claimed in claim 1, wherein the intermediate panel is formed of a material having greater elasticity than a material on an opposing side of the first and the second fasteners or in a remainder of the garment.

14. The medical compression garment as claimed in claim 1, wherein the first and the second fasteners are provided on a first or a front side of the garment and a further fastener is provided on a second or a rear side of the garment.

15. The medical compression garment as claimed in claim 1, wherein the garment is arranged to surround the upper arms of the wearer.

16. A medical compression garment as claimed in claim 14, wherein the garment further comprises a fourth elongate fastener provided on the same side as the third fastener but spaced apart therefrom.

17. A medical compression garment as claimed in claim 8, wherein the auxiliary fastener and the first or second fastener are provided on a front side of the garment.

18. A medical compression garment as claimed in claim 8, wherein the auxiliary fastener extends from the neck opening to a leg opening of the garment.

* * * * *